(12) United States Patent
Zhang et al.

(10) Patent No.: US 10,858,408 B2
(45) Date of Patent: Dec. 8, 2020

(54) TRANSDERMAL PEPTIDE WITH NUCLEAR LOCALIZATION ABILITY AND USE THEREOF

(71) Applicant: SOOCHOW UNIVERSITY, Suzhou (CN)

(72) Inventors: Shuyu Zhang, Suzhou (CN); Jianping Cao, Suzhou (CN); Daojiang Yu, Suzhou (CN); Wei Zhu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 16/484,153

(22) PCT Filed: Sep. 30, 2017

(86) PCT No.: PCT/CN2017/105051
§ 371 (c)(1),
(2) Date: Aug. 7, 2019

(87) PCT Pub. No.: WO2019/047299
PCT Pub. Date: Mar. 14, 2019

(65) Prior Publication Data
US 2020/0002389 A1 Jan. 2, 2020

(30) Foreign Application Priority Data
Sep. 5, 2017 (CN) .......................... 2017 1 0790765

(51) Int. Cl.
| | | |
|---|---|---|
| *A61K 38/17* | (2006.01) |
| *A61K 38/16* | (2006.01) |
| *A61K 38/00* | (2006.01) |
| *A61K 49/00* | (2006.01) |
| *A61K 47/62* | (2017.01) |
| *A61P 17/00* | (2006.01) |
| *C07K 14/47* | (2006.01) |
| *C07K 14/00* | (2006.01) |
| *C12N 9/02* | (2006.01) |

(52) U.S. Cl.
CPC .............. *C07K 14/47* (2013.01); *A61K 47/62* (2017.08); *A61K 49/0043* (2013.01); *A61K 49/0056* (2013.01); *A61P 17/00* (2018.01); *C12N 9/0089* (2013.01); *C12Y 115/01001* (2013.01); *A61K 38/00* (2013.01); *C07K 2319/60* (2013.01)

(58) Field of Classification Search
CPC ........ A61K 38/17; A61K 49/00; A61K 38/16; A61K 47/62; A61K 49/0043; A61K 49/0056; A61K 38/00; A61P 17/00; C07K 14/47; C07K 14/435; C07K 14/00; C07K 2319/09; C07K 2319/60
USPC ................. 514/1.1, 18.6, 21.4; 530/300, 326
See application file for complete search history.

(56) References Cited

U.S. PATENT DOCUMENTS

| | | | |
|---|---|---|---|
| 10,287,547 B2 * | 5/2019 | Ding ....................... C07K 16/40 |
| 2005/0100979 A1 | 5/2005 | Power | |
| 2017/0037366 A1 * | 2/2017 | Ding ....................... C07K 16/40 |

FOREIGN PATENT DOCUMENTS

CN 102485272 A 6/2012

OTHER PUBLICATIONS

P30041 from UniProt, pp. 1-10. INtegrated into UniProtKB/Swiss-Prot on Apr. 1, 1993. (Year: 1993).*
Fujii et al., Augmented expression of peroxiredoxin VI in rat lung and kidney after birth implies an antioxidative role, Eur. J. Biochem. 268, 218-224, Sep. 15, 2003.
GenBank Acession No. NP-004896.1, May 7, 1999.

* cited by examiner

*Primary Examiner* — Julie Ha
(74) *Attorney, Agent, or Firm* — SZDC Law P.C.

(57) ABSTRACT

A transdermal peptide with a nuclear localization ability and having an amino acid sequence as shown in SEQ ID NO: 1 is disclosed. A fusion protein including a macromolecular protein with one end being linked to the transdermal peptide is also disclosed. The transdermal peptide can be used in the preparation of a medicament or a transdermal preparation for treating skin diseases. A medicament for treating a skin disease includes the transdermal peptide and a pharmaceutically acceptable excipient. The transdermal peptide enters the cells autonomously to locate in the nuclei, and can penetrate through the stratum corneum of the skin into cells in the dermis. The peptide is conveniently synthesized artificially and suitable for transdermal administration, and has a therapeutic potential via transdermal administration by carrying a drug for treating skin diseases.

4 Claims, 3 Drawing Sheets
Specification includes a Sequence Listing.

SEQUENCE LISTING

```
<160> NUMBER OF SEQ ID NOS: 3

<210> SEQ ID NO 1
<211> LENGTH: 21
<212> TYPE: PRT
<213> ORGANISM: Artificial sequence
<220> FEATURE:
<223> OTHER INFORMATION: Transdermal peptide

<400> SEQUENCE: 1

Lys Lys Leu Phe Pro Lys Gly Val Phe Thr Lys Glu Leu Pro Ser
                5                   10                  15

Gly Lys Lys Tyr Leu Arg
            20

<210> SEQ ID NO 2
<211> LENGTH: 198
```

```
<212> TYPE: PRT
<213> ORGANISM: Artificial sequence
<220> FEATURE:
<223> OTHER INFORMATION: Macromolecular protein

<400> SEQUENCE: 2

Met Pro Gly Gly Leu Leu Leu Gly Asp Val Ala Pro Asn Phe Glu
                 5                  10                  15

Ala Asn Thr Thr Val Gly Arg Ile Arg Phe His Asp Phe Leu Gly
                20                  25                  30

Asp Ser Trp Gly Ile Leu Phe Ser His Pro Arg Asp Phe Thr Pro
                35                  40                  45

Val Cys Thr Thr Glu Leu Gly Arg Ala Ala Lys Leu Ala Pro Glu
                50                  55                  60

Phe Ala Lys Arg Asn Val Lys Leu Ile Ala Leu Ser Ile Asp Ser
                65                  70                  75

Val Glu Asp His Leu Ala Trp Ser Lys Asp Ile Asn Ala Tyr Asn
                80                  85                  90

Cys Glu Glu Pro Thr Glu Lys Leu Pro Phe Pro Ile Ile Asp Asp
                95                 100                 105

Arg Asn Arg Glu Leu Ala Ile Leu Leu Gly Met Leu Asp Pro Ala
               110                 115                 120

Glu Lys Asp Glu Lys Gly Met Pro Val Thr Ala Arg Val Val Phe
               125                 130                 135

Val Phe Gly Pro Asp Lys Lys Leu Lys Leu Ser Ile Leu Tyr Pro
               140                 145                 150

Ala Thr Thr Gly Arg Asn Phe Asp Glu Ile Leu Arg Val Val Ile
               155                 160                 165

Ser Leu Gln Leu Thr Ala Glu Lys Arg Val Ala Thr Pro Val Asp
               170                 175                 180

Trp Lys Asp Gly Asp Ser Val Met Val Leu Pro Thr Ile Pro Glu
               185                 190                 195

Glu Glu Ala

<210> SEQ ID NO 3
<211> LENGTH: 20
<212> TYPE: PRT
<213> ORGANISM: Artificial sequence
<220> FEATURE:
<223> OTHER INFORMATION: Control polypeptide

<400> SEQUENCE: 3

Ile Ala Leu Ser Ile Asp Ser Val Glu Asp His Leu Ala Trp Ser
                 5                  10                  15

Lys Asp Ile Asn Ala
                20
```

TRANSDERMAL PEPTIDE WITH NUCLEAR LOCALIZATION ABILITY AND USE THEREOF

This application is the National Stage Application of PCT/CN2017/105051, filed on Sep. 30, 2017, which claims priority to Chinese Patent Application No.: CN 201710790765.3, filed on Sep. 5, 2017, which is incorporated by reference for all purposes as if fully set forth herein.

FIELD OF THE INVENTION

The present invention relates to the field of biological technology, and more particularly to a transdermal peptide with nuclear localization ability and use thereof.

DESCRIPTION OF THE RELATED ART

The skin is the largest organ in the human body. It covers the surface of the whole body, accounts for about 16% of the body weight, and has a total area of up to 1.2 to 2 square meters. The skin consists of the epidermis layer, the dermis layer and the subcutaneous tissue, and is rich in blood vessels, nerves and various skin appendages, including hair, hair follicles, sweat glands, and sebaceous glands. It is the body's first line of defense, preventing the tissues and internal organs from being attacked by external physical, chemical, and biological stimuli. In addition, the skin also has the functions of immune, stimulus perception, body temperature regulation, absorption, secretion and excretion. The stratum corneum is the outermost part of the epidermis and consists essentially of 10-20 layers of flat, dead cells without nuclei. When these cells fall off, the underlying cells in the basal stratum are pushed up to form a new stratum corneum. The function of the stratum corneum is to protect the skin physically, mechanically, chemically and biologically against damage from harmful substances and to maintain the function integrity by blocking the entry of most macromolecular substances. However, the barrier of the stratum corneum also prevents the absorption, by the epidermis and the dermal tissue, of exogenous nutrients and drugs supplied through the epidermis.

Transdermal penetration enhancers are one class of compounds which can accelerate the penetration of external drugs through the skin, such as pyrrolidones, azones, terpenoids, esters of amino acids and the like. However, the existing transdermal penetration enhancing compounds have a short duration of action, are susceptible to metabolization, have a poor transdermal effect, have skin toxicity at a high concentration, and have little effect on the transdermal penetration of biological macromolecules such as proteins.

Because macromolecular proteins and polypeptide drugs are hydrophilic macromolecules, they can hardly penetrate the lipophilic barrier of the stratum corneum of the skin. Even with the help of transdermal penetration enhancers, protein molecules with a molecular weight of greater than 500 Da are difficult to penetrate through the stratum corneum. Therefore, transdermal administration of biologically active macromolecular proteins has not been solved for a long time. How to enable biological macromolecules with important value to be administered through the epidermal route has become a difficult and hot topic of research. Extensive research is performed on the transdermal penetration of proteins mediated by physical methods, including ultrasonic method, electric shock, and microneedle, etc. However, because of the dependence of the above methods on equipment, it is difficult to put them into large-scale applications.

The use of peptide-mediated transdermal penetration of proteins has attracted wide attention in recent years. After finding a new peptide that can mediate the transdermal penetration of macromolecules, it is expected that relevant diseases can be treated by transdermal administration by linking functional proteins, polypeptides and compounds to the transdermal peptide. Therefore, it is of great practical significance to provide a transdermal peptide with a nuclear localization ability.

The nucleus is the largest and most important organelle in eukaryotic cells, the regulatory center of cell heredity and metabolism, and one of the most notable markers of eukaryotic cells distinguished from prokaryotic cells. Both the cell membrane and the nuclear membrane are selectively permeable membranes, which provide a protection for the cells and cell nuclei, and also prevent the entry of functional cells and nuclear protective molecules. Therefore, screening peptides that can mediate the entry of key molecules into the cell membrane and nuclear membrane and be localized in the nucleus is of great significance for delivering important molecules to protect the nucleus. However, there are no reports of peptides with both nuclear localization and transdermal penetration abilities.

SUMMARY OF THE INVENTION

In order to solve the above technical problems, an object of the present invention is to provide a transdermal peptide having a nuclear localization ability and use thereof. The transdermal peptide of the present invention can enter the cell autonomously and be located in the nucleus, and can penetrate through the stratum corneum of the skin into cells in the dermis. The peptide is conveniently synthesized artificially and can be administered transdermally.

The present invention provides a transdermal peptide with a nuclear localization ability, which has an amino acid sequence as shown in SEQ ID NO: 1, and can enter the eukaryotic cells autonomously.

Preferably, the transdermal peptide is further linked to fluorescein.

Preferably, the fluorescein is fluorescein isothiocyanate (FITC), rhodamine or carboxyfluorescein (FAM).

Preferably, the eukaryotic cells are HaCaT cells, WS1 cells, TE-1 cells, Eca-109 cells, HeLa cells or primary skin cells.

The transdermal peptide with a nuclear localization ability has an isoelectric point of 10.92 and a molecular weight of 2465 Da.

The transdermal peptide enters eukaryotic cells in a dose-dependent and time-dependent manner, and can successfully enter the cells at a concentration of 0.1-10 µmol/L after 0.1-240 min.

The present invention further provides a fusion protein with a nuclear localization ability, which comprises a macromolecular protein, one end of which is linked to the above-described transdermal peptide (having an amino acid sequence as shown in SEQ ID NO: 1) with a nuclear localization ability.

Preferably, the transdermal peptide is further linked to fluorescein.

Preferably, the other end of the macromolecular protein is linked to a fluorescent protein.

Preferably, the fluorescent protein is enhanced green fluorescent protein (EGFP).

Preferably, the molecular weight of the macromolecular protein is 10-50 KD.

Preferably, the macromolecular protein has an amino acid sequence as shown in SEQ ID NO: 2; or the macromolecular protein is human superoxide dismutase 1 (SOD1).

The present invention also discloses the use of the transdermal peptide (having an amino acid sequence as shown in SEQ ID NO: 1) with a nuclear localization ability in the preparation of a medicament or a transdermal preparation for treating skin diseases.

Preferably, the skin disease is skin injury, and more preferably, the skin disease is radiation skin injury.

Preferably, the transdermal peptide is further linked to fluorescein.

The present invention also provides a medicament for treating a skin disease, comprising the transdermal peptide with a nuclear localization ability and a pharmaceutically acceptable excipient.

Preferably, the dosage form of the medicament for treating a skin disease is a water extract, a powder, a lotion, a tincture, an oily agent, a cream, an ointment, a plaster or an aerosol.

By means of the above technical solution, the present invention has the following advantages.

The transdermal peptide disclosed in the present invention has the ability to localize into the nucleus after entering the cell autonomously on one hand; and has transdermal penetration ability and can penetrate through the stratum corneum of the skin into the cells in the dermis on the other hand. The short peptide has a small molecular weight, is convenient for artificial synthesis, and can be administered through the epidermis, and has the potential to carry transdermal therapeutic drugs for treating skin diseases.

After the transdermal peptide is fused with a macromolecular protein, the obtained fusion protein can enter the cells and be localized in the nuclei, indicating that the transdermal peptide of the present invention has the function of carrying the macromolecular protein linked thereto to enter the cells and being localized in the nuclei.

These and other objects and advantages of the present invention will become readily apparent to those skilled in the art upon reading the following detailed description by referring to the accompanying drawings.

DETAILED DESCRIPTION OF THE PREFERRED EMBODIMENTS

The invention will be further illustrated in more detail with reference to the accompanying drawings and embodiments. It is noted that, the following embodiments only are intended for purposes of illustration, but are not intended to limit the scope of the present invention.

Example 1

The raw materials and reagents for the transdermal peptide with a nuclear localization ability provided in the present invention are commercially available.

Figure 1:
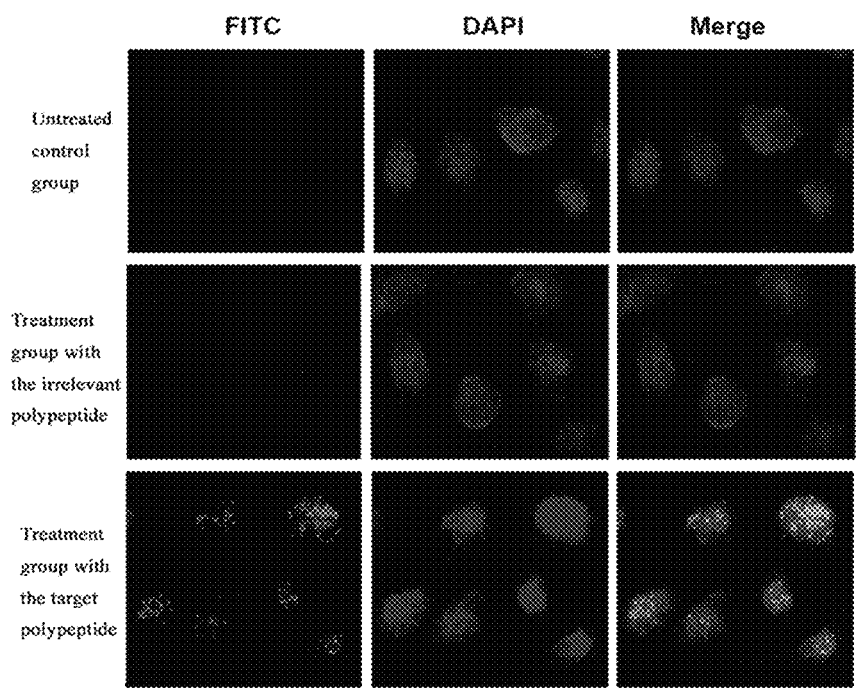
FIG. 1 shows the detection results of abilities to enter HaCaT cells and localize in the nuclei of the transdermal peptide of the present invention and the control peptide after labeling with FITC.

A peptide having an N terminus labeled with FITC was synthesized by the fmoc method, which has an amino acid sequence as shown in SEQ ID NO: 1. The synthesized peptide was dissolved in a phosphate buffer (PBS, pH=7.4) to prepare a solution having a concentration of 500 µmol/L. HaCaT cells were cultured in vitro, and when the cells were grown to a cell density of 50%, the polypeptide solution was added to the medium at a final concentration of 10 µmol/L. After 4 hrs, DAPI was added for nuclear staining for 30 min. The culture medium was discarded, the cells were rinsed three times with PBS, and photographed under a confocal fluorescence microscope after the free fluorescent polypeptide was removed. For comparison, a control polypeptide as shown in SEQ ID NO: 3 was synthesized using the above method, where the N-terminus of the control polypeptide was also labeled with FITC. The fluorescence intensity was tested by culturing the cells with the control polypeptide according to the above method. The results of comparison with the untreated control cells are shown in FIG. 1. FIG. 1 shows that a green fluorescent signal can be observed in the nuclei of the cells (the treatment group with the target polypeptide) to which the peptide of the present invention is added, and there is no green fluorescence in the cells added with the irrelevant control polypeptide (the treatment group with the irrelevant polypeptide), indicating that the peptide of the present invention has a function of entering HaCaT cells.

Example 2

Figure 2:
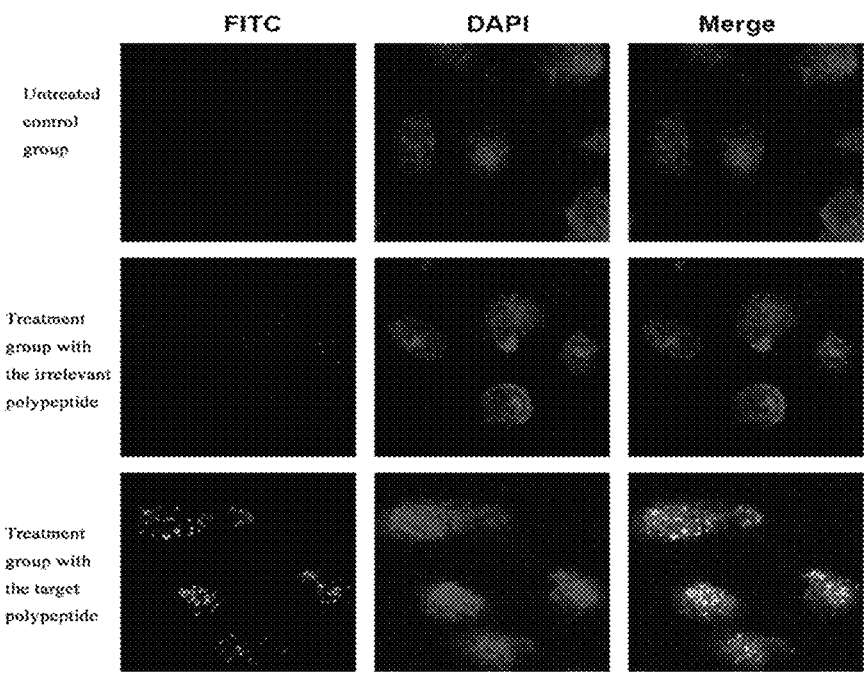
FIG. 2 shows the detection results of abilities to enter WS1 cells and localize in the nuclei of the transdermal peptide of the present invention and the control peptide after labeling with FITC.

The transdermal peptide of the present invention and the control polypeptide were synthesized according to the method as described in Example 1, and the N-termini of both polypeptides were labeled with FITC. The human fibroblasts WS1 were cultured following the method as described in Example 1, and when the cells were grown to a cell density of 50%, the polypeptide solution or the control polypeptide solution was added to the medium at a final concentration of 10 µmol/L. After 4 hrs, DAPI was added for nuclear staining for 30 min. The culture medium was discarded, the cells were rinsed three times with PBS, and photographed under a confocal fluorescence microscope after the free fluorescent polypeptide was removed. The results of comparison with the untreated control cells are shown in FIG. 2. FIG. 2 shows that a green fluorescent signal can be observed in the nuclei of the cells (the treatment group with the target polypeptide) to which the peptide of the present invention is added, and there is no green fluorescence in the cells added with the irrelevant control polypeptide (the treatment group with the irrelevant polypeptide), indicating that the peptide of the present invention has a function of entering WS1 cells.

Example 3

Figure 3:
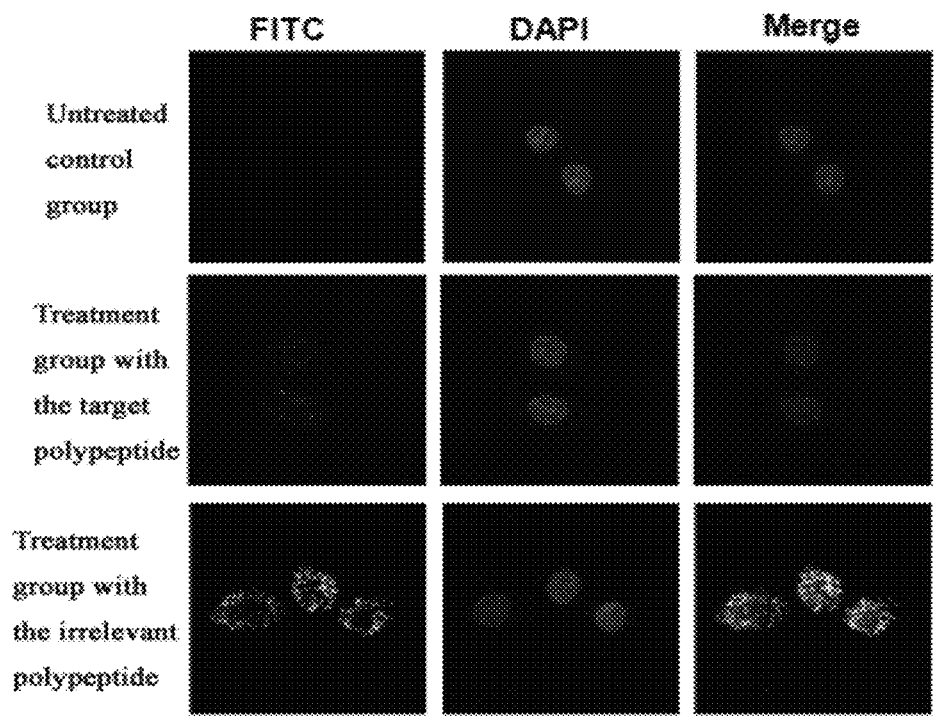
FIG. 3 shows the detection results of abilities to enter TE-1 cells and localize in the nuclei of the transdermal peptide of the present invention and the control peptide after labeling with FITC.

The transdermal peptide of the present invention and the control polypeptide were synthesized according to the method as described in Example 1, and the N-termini of both polypeptides were labeled with FITC. The TE-1 cells were cultured following the method as described in Example 1, and when the cells were grown to a cell density of 50%, the polypeptide solution or the control polypeptide solution was added to the medium at a final concentration of 10 μmol/L. After 4 hrs, DAPI was added for nuclear staining for 30 min. The culture medium was discarded, the cells were rinsed three times with PBS, and photographed under a confocal fluorescence microscope after the free fluorescent polypeptide was removed. The results of comparison with the untreated control cells are shown in FIG. 3. FIG. 3 shows that a green fluorescent signal can be observed in the nuclei of the cells (the treatment group with the target polypeptide) to which the peptide of the present invention is added, and there is no green fluorescence in the cells added with the irrelevant control polypeptide (the treatment group with the irrelevant polypeptide), indicating that the peptide of the present invention has a function of entering TE-1 cells.

Example 4

The transdermal peptide of the present invention was synthesized according to the method as described in Example 1, and the N-terminal of the polypeptide was labeled with FITC. The HaCaT cells were cultured in multiple petri dishes following the method as described in Example 1, and when the cells were grown to a cell density of 50%, the polypeptide solution was added to the medium at a final concentration of 0 μmol/L, 3 μmol/L, 6 μmol/L, and 10 μmol/L respectively. After 4 hrs, DAPI was added for nuclear staining for 30 min. The culture medium was discarded, the cells were rinsed three times with PBS, and photographed under a confocal fluorescence microscope after the free fluorescent polypeptide was removed.

Figure 4:
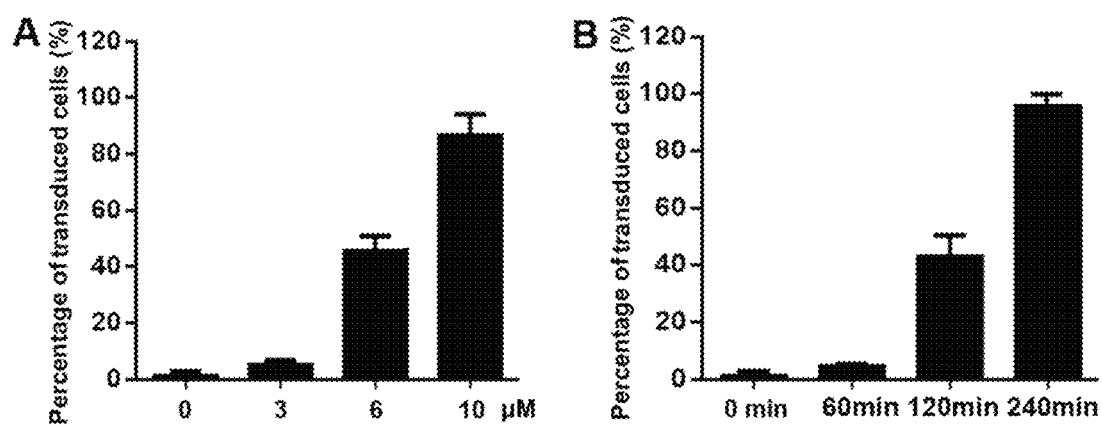
FIG. 4 shows the detection results of the dose and time dependence of the percentages of the transdermal peptide of the present invention entering HaCaT cells after labeling with FITC.

Alternatively, after the cells were grown to a cell density of 50%, the polypeptide solution was added to the medium at a final concentration of 10 μmol/L, and after 0, 60, 120, and 240 min, DAPI was added for nuclear staining for 30 min. The culture medium was discarded, the cells were rinsed three times with PBS, and photographed under a confocal fluorescence microscope after the free fluorescent polypeptide was removed. The results are shown in FIG. 4. The percentage of cells having fluorescence signal in the nuclei of the cells to which the peptide of the present invention is added is dose-dependent (shown in FIG. 4A) and time dependent (shown in FIG. 4B). As the dose of the polypeptide increases and the time elapse, more polypeptide enters the cells.

Example 5

Figure 5:
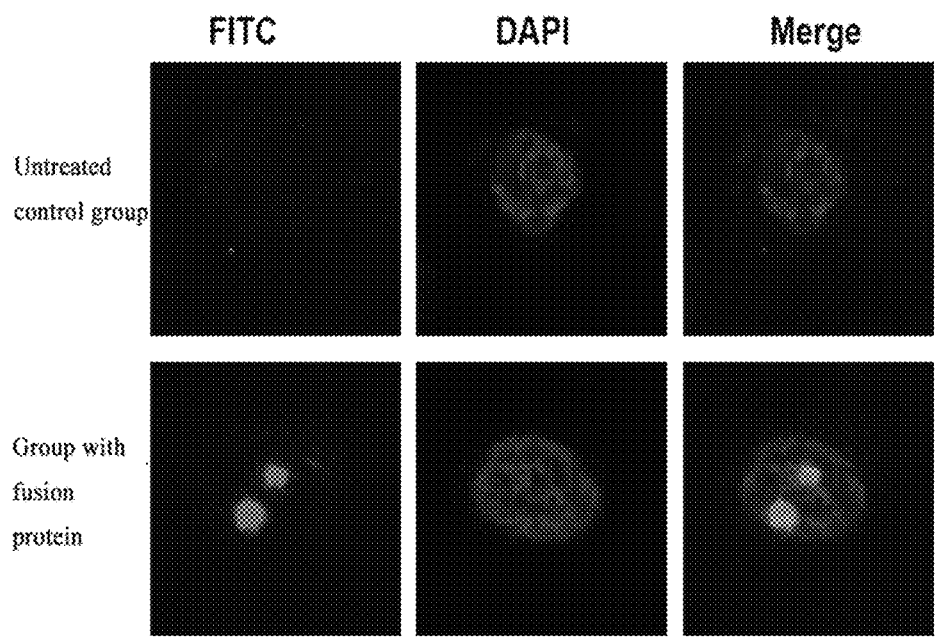
FIG. 5 shows the test result of the fusion protein of the present invention entering HaCaT cells and being localized into the nuclei.

This example provides a fusion protein and the abilities of the fusion protein to enter the cells and localize in the nuclei are detected. The specific method is as follows.
1. Construction of Gene of Coupled Protein Fused With Peptide With Nuclear Localization and Transdermal Penetration Abilities
A peptide (having an amino acid sequence as shown in SEQ ID NO: 1) with nuclear localization and transdermal penetration abilities, and a fusion protein of a protein as shown in SEQ ID NO: 2 with enhanced green fluorescent protein (EGFP) were constructed. The gene encoding the above protein is in the middle, the EGFP encoding gene is located at the N terminus, and the gene encoding the peptide with nuclear localization and transdermal penetration abilities is located at the C terminus. The nucleic acid was designed and synthesized according to the sequence of the polypeptide and the protein, and then inserted into the pET-28a vector (Novagen, USA) to construct pET-28a-EGFP-pep, and the inserted sequence was sequenced and identified to be correct.
2. Expression of Fusion Gene in $E.\ coli$
$E.\ coli$ BL21 (DE3) was transformed with the constructed vector pET-28a-EGFP-pep. When the bacterial solution was grown to an $OD_{600}$ of 0.6, IPTG (final concentration: 1 mmol/L) was added to perform induction at 30° C. for 10 hrs.
3. Purification of Fusion Protein
The bacteria solution induced to expression was treated for 1 hr by adding a lysozyme, ultrasonically homogenized, and centrifuged at 12,000 rpm for 30 minutes at 4° C. The expression product was dissolved in the supernatant. After centrifugation, the supernatant was transferred to a 10 mL Eppendorf tube, and Ni-NTA (Novagen, USA) was added, and shaken at 50 rpm for 2 h at 4° C. The above mixture was transferred to a chromatographic column, and 4 ml of Wash Buffer (containing PBS and 0.1 M imidazole) was added to wash the chromatographic column when the liquid was running out. When the liquid was almost completely flowed through, 300 μL of an eluate (containing PBS and 0.4 M imidazole) was added, and the efflux protein peak was collected under a nucleic acid/protein detector. The purified liquid was subjected to SDS-PAGE analysis and the molecular weight was about 50 KD, which was consistent with the calculated value. Through the above method, a fusion protein with a purity of over 90% can be obtained.
4. Detection of Abilities to Enter Cells and Localize in Nuclei of Fusion Protein
HaCaT cells were cultured in vitro, and when the cells were grown to a cell density of 50%, the purified fusion protein was added to the medium at a final concentration of 10 μmol/L. After 4 hrs, DAPI was added for nuclear staining for 30 min. The cells were rinsed three times with PBS, and photographed under a confocal fluorescence microscope after the free fusion protein was removed. The results show that after adding the peptide of the present invention fused to the fusion protein of the polypeptide and EGFP, a green fluorescent signal is observed in the nuclei of HaCaT cells (FIG. 5), indicating that the peptide has the function of carrying a macromolecular protein molecule attached thereto to enter the cells and localize in the nuclei.

Example 6

Figure 6:
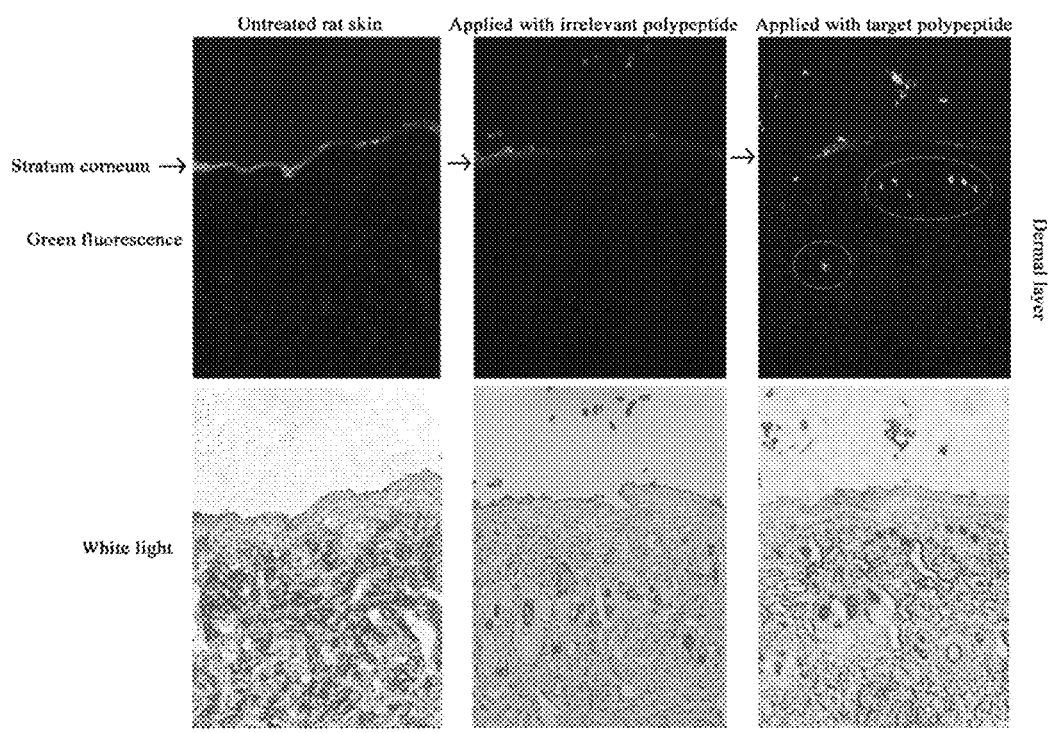
FIG. 6 is a schematic view showing the results of the transdermal penetration effect of the transdermal peptide of the present invention.

In this example, the transdermal penetration effect of the peptide was detected through the following specific method.
The experiments were performed using 8-week old SD rats (body weight 250 g). The back of SD rats was shaved, and the FITC-labeled peptide and control peptide prepared in Example 1 were each dissolved in a phosphate buffer (PBS, pH=7.4) to prepare a solution having a concentration of 500 μmol/L. The SD rats were divided into three groups, including: 1) a control group, in which no polypeptide solution was applied on the back; 2) a control group, in which the peptide as shown in SEQ ID NO: 3 was applied on the dorsal epidermis of rats; and 3) a treatment group, in which the peptide as shown in SEQ ID NO: 1 was applied on the back skin of rats. The rats in Groups 2) and 3) were each applied with 50 μL of the polypeptide solution. After three hours, the polypeptide in the applied area was washed off; the SD rats were sacrificed, and the skin applied with the polypeptide was taken, frozen, sectioned, and then observed under a fluorescence microscope. The test results show that there is no green fluorescence in the dermal tissue of the skin of the control group (untreated rat skin) and the control peptide group (control group applied with irrelevant polypeptide) (the arrow in FIG. 6 indicates the stratum corneum with autofluorescence). In the skin section of rats coated with the peptide of the present invention (the polypeptide of interest), a fluorescent signal (the fluorescent signal shown in the ellipse in FIG. 6) is clearly observed in the skin appendages of the dermis, indicating that the peptide can transdermally penetrate into the dermal tissue.

Example 7

The transdermal peptide (with an amino acid sequence as shown in SEQ ID NO: 1) of the present invention was used in the preparation of a medicament for treating skin diseases, and was prepared as a water extract after adding a conventional excipient.

The transdermal peptide (with an amino acid sequence as shown in SEQ ID NO: 1) of the present invention was fused with human superoxide dismutase 1 (SOD1), expressed, and then applied once a day to the mice from which the epidermis on the back was removed. The control group was applied with SOD1 not linked to the polypeptide of the present invention. The results show that after three days, the wounds of the rats in the experimental group are reduced by 38% compared with the control group, indicating that the peptide of the present invention mediates the entry of SOD1 into cells to effectively treat skin wounds.

Example 8

The transdermal peptide (with an amino acid sequence as shown in SEQ ID NO: 1) of the present invention was used in the preparation of a medicament for treating skin diseases, and was prepared as a powder after adding a conventional excipient.

Example 9

The transdermal peptide (with an amino acid sequence as shown in SEQ ID NO: 1) of the present invention was used in the preparation of a medicament for treating skin diseases, and was prepared as an oily agent after adding a conventional excipient.

Example 10

The transdermal peptide (with an amino acid sequence as shown in SEQ ID NO: 1) of the present invention was used in the preparation of a medicament for treating skin diseases, and was prepared as a cream after adding a conventional excipient.

Example 11

The transdermal peptide (with an amino acid sequence as shown in SEQ ID NO: 1) of the present invention was used in the preparation of a medicament for treating skin diseases, and was prepared as an ointment after adding a conventional excipient.

Example 12

The transdermal peptide (with an amino acid sequence as shown in SEQ ID NO: 1) of the present invention was used in the preparation of a medicament for treating skin diseases, and was prepared as a plaster after adding a conventional excipient.

Example 13

The transdermal peptide (with an amino acid sequence as shown in SEQ ID NO: 1) of the present invention was used in the preparation of a medicament for treating skin diseases, and was prepared as an aerosol after adding a conventional excipient.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. An isolated transdermal peptide with a nuclear localization ability, having an amino acid sequence as shown in SEQ ID NO: 1 and being linked to a fluorescein, wherein the transdermal peptide enters the eukaryotic cells autonomously.

2. The isolated transdermal peptide according to claim 1, wherein the fluorescein is fluorescein isothiocyanate, rhodamine or carboxyfluorescein (FAM).

3. The isolated transdermal peptide according to claim 1, wherein the eukaryotic cells are HaCaT cells, WS1 cells, TE-1 cells, Eca-109 cells, or HeLa cells.

4. A medicament for treating a skin disease, comprising the isolated transdermal peptide according to claim 1 and a pharmaceutically acceptable excipient.

* * * * *